United States Patent [19]  [11] 4,141,993
Carnmalm et al. [45] Feb. 27, 1979

[54] COMPOUNDS OF DIPHENYLCYCLOPENTYLAMINE TYPE AND METHODS FOR THEIR PREPARATION

[75] Inventors: Bernt S. E. Carnmalm; Ulf H. A. Lindberg, both of Södertalje; Tomas De Paulis, Gnesta; Svante B. Ross, Södertalje; Nils-Erik Stjernstrom, Södertalje; Carl B. J. Ulff, Södertalje; Sven-Ove Ogren, Södertalje, all of Sweden

[73] Assignee: Astra Läkemedel Aktiebolaget, Södertalje, Sweden

[21] Appl. No.: 798,446

[22] Filed: May 19, 1977

Related U.S. Application Data

[60] Division of Ser. No. 579,049, May 20, 1975, Pat. No. 4,053,637, which is a continuation of Ser. No. 257,707, May 30, 1973, abandoned.

[30] Foreign Application Priority Data

Jun. 11, 1971 [SE] Sweden ............................... 717632

[51] Int. Cl.$^2$ .......................... A01N 9/20; A01N 9/24
[52] U.S. Cl. .................. 424/330; 260/501.1; 260/501.12; 260/501.18; 260/501.19; 260/501.21; 260/544 N; 260/558 R; 260/570 R; 260/571; 260/576; 260/578; 424/316
[58] Field of Search ........... 260/570 R, 501.1, 501.12; 424/316, 330

[56] References Cited

U.S. PATENT DOCUMENTS 3,285,960  11/1966  Halverstadt ........................ 260/570
3,328,249   6/1967  Aceto et al. ..................... 260/570 X
3,376,312   4/1968  Unger et al. ..................... 260/570 X Primary Examiner—Robert V. Hines
Attorney, Agent, or Firm—Brumbaugh, Graves, Donohue & Raymond

[57] ABSTRACT

Compounds of the formula

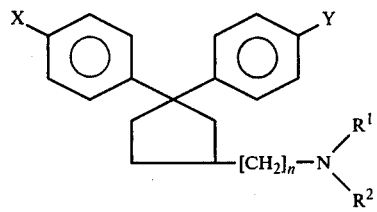

and pharmaceutically acceptable salts thereof, wherein X and Y are the same or different and each represents a hydrogen atom, a chloro or a methoxy group, n is an integer 0 or 1 and $R^1$ and $R^2$ are the same or different and each representing a hydrogen atom or a methyl group; processes for their preparation; pharmaceutical preparations containing at least one of these compounds and the use thereof in the treatment of depressive states.

40 Claims, No Drawings

COMPOUNDS OF DIPHENYLCYCLOPENTYLAMINE TYPE AND METHODS FOR THEIR PREPARATION

This application is a division of application Ser. No. 579,049 filed May 20, 1975 and now U.S. Pat. No. 4,053,637, which in turn was a continuation of application Ser. No. 257,707 filed May 30, 1973, now abandoned. The benefit of the filing dates of applications Nos. 257,707 and 579,049 is hereby claimed pursuant to 35 U.S.C. Sec. 120 and 121.

This invention relates to new compounds of the diphenylcyclopentylamine type and methods for their preparation. The invention also relates to the preparation of pharmaceutical preparations containing such compounds and to methods for the pharmacological use of the compounds.

The main object of the invention is to provide compounds having psychopharmacological, especially antidepressive properties.

Depressions are considered to depend on changes in the biochemical processes of the brain which control the mood. The nature of this biochemical deficiency is largely unknown but in depressive states there is evidence for a decreased activity of monoaminergic brain neurons. The monoamines, noradrenaline (NA), dopamine (DA) and 5-hydroxytryptamine (5-HT), are of great interest in this respect.

It has been demonstrated that NA, DA and 5-HT are localized in three different types of neurones and may function as transmittors in the central nervous system. The monoamines are stored in special structure, granules, situated in enlargements of the nerve endings, varicosities. The varicosity is separated from the effector neuron by a space, the synaptic cleft or spatium. As a result of a nerve stimulation, the transmittor is released from the granule into the synaptic cleft and reaches the receptor of the effector neuron and generates a nerve impulse. After impulse generation, the amines are inactivated by mainly two mechanisms: a re-uptake mechanism at the cell membrane and enzymatic conversion by cathechol-O-methyltransferase to form methylated metabolites. There is also an inactivating enzyme within the varicosities, monoamine oxidase (MAO), that is stored in the mitochondria and inactivates the amines intracellularly.

When MAO-inhibitors are administered, an increased amount of transmittor substance becomes available for release at the nerve ending.

Another way of increasing the amine levels at the receptor is exerted by the tricyclic antidepressants. It has been shown that this type of compound inhibits the re-uptake mechanism of NA and 5-HT, and the antidepressive action is assumed to be related to the uptake inhibition of NA and 5-HT.

The overall clinical effect of the tricyclic anti-depressants consists according to Keilholz (Deutsch Med. Wschr. 93, 1968) of three main components in various proportions:

1. Psychomotor activating or increase in drive
2. Elevation of mood
3. Relief of anxiety.

It has been proposed that the correlation between the clinical effects and the biochemical changes in the adrenergic neurones might be that the NA neurones are involved in psychomotor activity and the 5-HT-neurones are involved in the elevation of mood. The third component, relief of anxiety, may be caused by blockade of the NA and DA receptors, but probably not the 5-HT receptors. However, it should be pointed out that these theories are much simplified.

A compound frequently used for controlling depressions is imipramine (Tofranil ®)

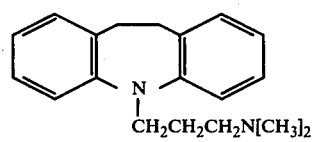

CH$_2$CH$_2$CH$_2$N[CH$_3$]$_2$

This compound is both mood elevating and psychomotor activating, but it possesses several disadvantages. It is anticholinergic and causes anticholinergic symptoms such as dryness of the mouth, tremor, tachycardia and sweating. In higher doses it can provide serious heart arrythmias and in normal doses it can cause toxic interactions in persons with heart failures. Furthermore, another drawback of treatment with imipramine is the late onset of the antidepressive effect which effect is observable first after 3 weeks of treatment.

According to the present invention, it has now been found that the above-mentioned disadvantages can be overcome by using compounds selected from the group consisting of compounds of the general formula

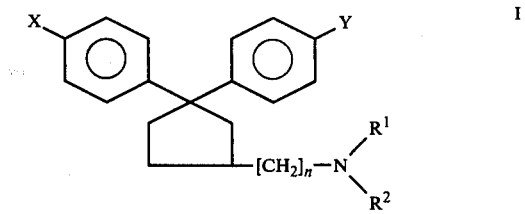

I wherein X and Y are the same or different and each representing a hydrogen atom, a chloro or a methoxy group, n is an integer 0 or 1, and R$^1$ and R$^2$ are the same or different and each representing a hydrogen atom or a methyl group, and pharmaceutically acceptable acid addition salts thereof.

The preferred compounds of the invention are those in which at least one of the groups X and Y is other than a hydrogen atom. Especially preferred is the compound 1-amino-3-(4-chlorophenyl)-3-phenylcyclopentane.

Compounds described above which contain an asymmetric carbon atom exist in the form of optically active forms, and can be resolved into their optical antipodes by well-known methods such as by using optically active acids such as tartaric acid, camphor-10-sulphonic acid, dibenzoyl tartaric acid and the like.

Some of the compounds described above can exist as stereoisomers, which forms constitute a further aspect of this invention. Mixtures of such isomers can be separated by methods known to the state of the art.

For example, the preferred compound, 1-amino-3-(4-chlorophenyl)-3-phenylcyclopentane, exhibits both optical and geometric isomerism. The optical isomerism results from the asymetric carbon atom attached to the amino group while the geometric isomerism results from the position of the chlorine substituted phenyl group with respect to the amino group.

The compounds described above can be used as mixtures of the above-mentioned isomeric forms or in the form of pure isomers.

The compounds of this invention with the general formula I can be prepared according to different methods.

A. The compounds of the invention with the general formula

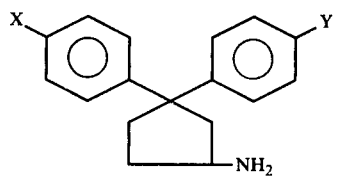

wherein X and Y have the meaning given above, can be obtained according to the reaction scheme

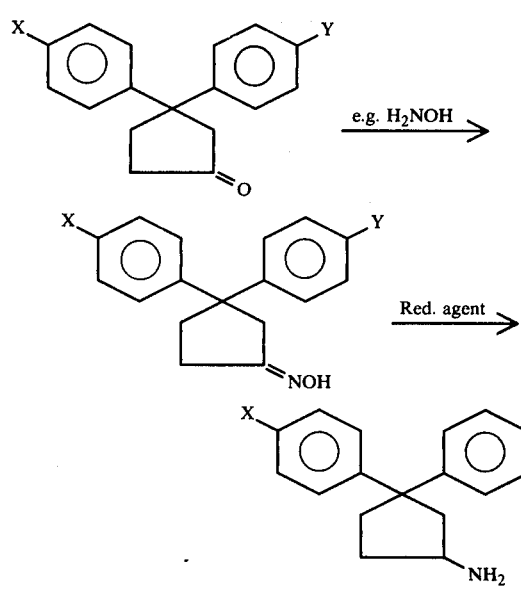

wherein X and Y have the meaning given above.

B. The compounds of the invention with the general formula

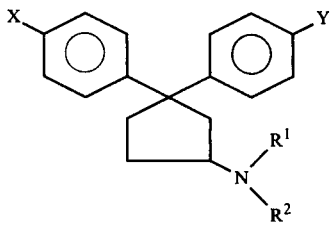

wherein X, Y, $R^1$ and $R^2$ have the meaning given above can be prepared according to the reaction scheme

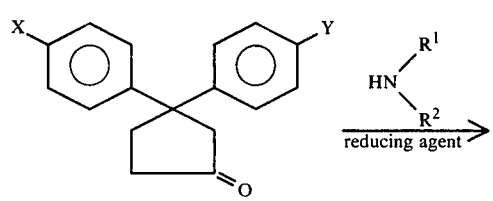

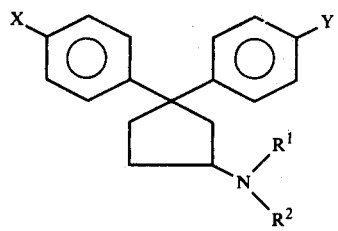

wherein X, Y, $R^1$ and $R^2$ have the meaning given above.

C. The compounds of the invention with the general formula

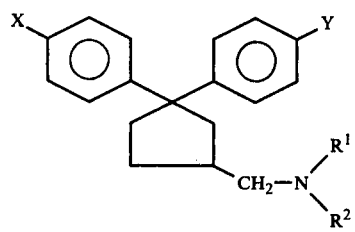

wherein X, Y, $R^1$ and $R^2$ have the meaning given above can be obtained according to the reaction scheme

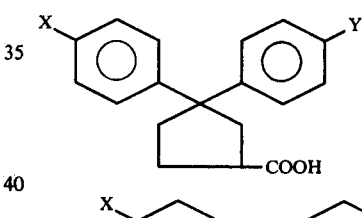

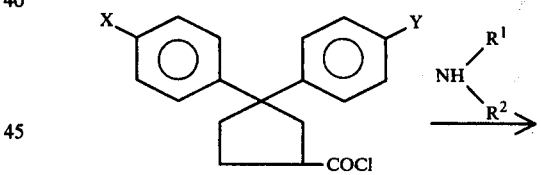

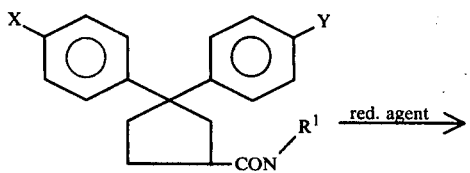

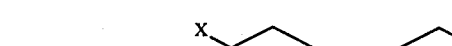

wherein X, Y, $R^1$ and $R^2$ have the meaning given above.

D. The compounds of the invention with the general formula

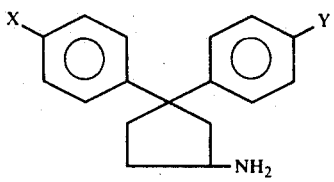

wherein X and Y have the meaning given above, can be obtained according to the reaction scheme

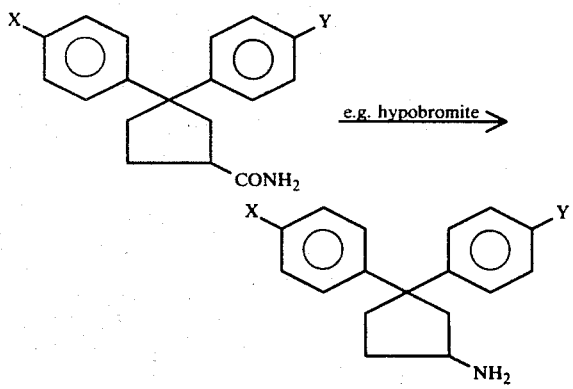

wherein X and Y have the meaning given above.

E. The compounds of the invention with the general formula

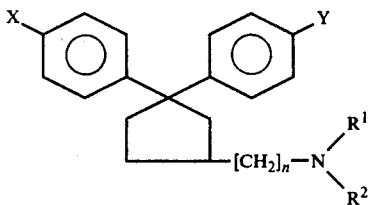

can be obtained by reacting a compound of the general formula

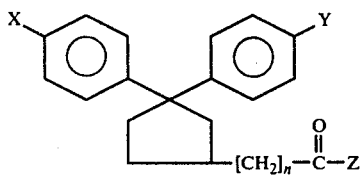

in which formulas X, Y, n, $R^1$ and $R^2$ have the previously given definition and Z is a hydroxy group, a halogen group, e.g. chlorine or another acid residue, e.g., an acid anhydride, with hydrozoic acid ($HN_3$) or an inorganic salt thereof according to the conditions of the Schmidt reaction, which gives a primary amine, and if a secondary or tertiary amine is desired converting the obtained primary amine in ways known per se to the corresponding secondary or tertiary amine.

In the cases where an intermediate acylic derivative or the like is obtained in any of the methods A - E hydrolysis is necessary to obtain the compounds of the formula I.

Both organic and inorganic acids can be employed to form non-toxic pharmaceutically acceptable acid addition salts of the compounds of this invention. Illustrative acids being sulfuric, nitric, phosphoric, hydrochloric, citric, acetic, lactic, tartaric, pamoic, ethanedisulfonic, sulfamic, succinic, cyclohexylsulfamic, fumaric, maleic and benzoic. These salts are readily prepared by methods known to the art.

In clinical practice the compounds of the present invention will normally be administered orally, or by injection, in the form of pharmaceutical preparations comprising the active ingredient either as a free base or as a pharmaceutically acceptable non-toxic, acid addition salt, e.g., the hydrochloride, lactate, acetate, sulfamate, and the like, in association with a pharmaceutically acceptable carrier. Accordingly, terms relating to the novel compounds of this invention, whether generically or specifically, are intended to include both the free amine base and the acid addition salts of the free base, unless the context in which such terms are used, e.g., in the specific examples, would be inconsistent with the broad concept. The carrier may be a solid, semisolid or liquid diluent or capsule. These pharmaceutical preparations constitute a further aspect of this invention. Usually the active substance will constitute between 0.1 and 95% by weight of the preparation, more specifically between 0.5 and 20% by weight for preparation intended for injection and between 2 and 50% by weight for preparations suitable for oral administration.

To produce pharmaceutical preparations containing a compound of the invention in the form of dosage units for oral application, the selected compound may be mixed with a solid fine grain carrier, e.g., lactose, saccharose, sorbitol, mannitol, starches such as potato starch, corn starch or amylopectin, cellulose derivatives, or gelatin and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g., gum arabic, gelatin, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatin capsules (pearl-shaped closed capsules) consisting of gelatin and, for example, glycerol or similar closed capsules, the active substance may be admixed with a vegetable oil. Hard gelatin capsules may contain granulates of the active substance in combination with solid, fine grain carriers such as lactose, saccharose, sorbitol, mannitol, starches (e.g. potato starch, corn starch or amylopectin), cellulose derivatives or gelatin.

Liquid preparations for oral application may be in the form of syrups or suspensions, for example, solutions containing from about 0.2% to about 20% by weight of the active substance herein described, the balance being sugar and a mixture of ethanol, water, glycerol and propyleneglycol. Optionally, such liquid preparations may contain coloring agents, flavoring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

In therapeutical treatment the suitable diurnal doses of the compounds of the invention are 5–500 mg for oral application, preferentially 50–250 mg and 1–100 mg for parenteral application, preferentially 10–50 mg.

The following examples will further illustrate the invention.

EXAMPLE 1

1-Amino-3,3-diphenylcyclopentane [PUB 105]

(a) 3,3-diphenylcyclopentanone (0.100 mole), hydroxylamine hydrochloride (0.250 mole), ethanol (100 ml) and pyridine (100 ml) were refluxed for two hours. The solvents were removed, water and chloroform added and the organic layer was separated. Chloroform was removed and the residue recrystallized from 90% ethanol. Yield 3,3-diphenylcyclopentanone oxime (85%). M.p. 113°–115° C.

(b) The oxime (0.100 mole) was dissolved in ether (500 ml) and cooled to 5° C. Lithium aluminum hydride (0.250 mole) was added portionwise and the mixture was refluxed for 2 hours. After cooling, saturated sodium sulfate solution (75 ml) was added dropwise and the white precipitate was filtered off. The ether solution was extracted with 1 N HCl, the acid solution made alkaline and extracted with ether. After removing the ether, the residual 1-amino-3,3-diphenylcyclopentane crystallized. M.p. 58°–60° C. Yield: 90% Hydrochloride: m.p. 181°–182° C.

According to the method described in Example 1, the following compounds were prepared:

1-amino-3-(4-chlorophenyl)-3-phenylcyclopentane/PUN 122/Hydrochloride m.p. 251°–254° C.

1-amino-3,3-di(4-chlorophenyl)cyclopentane/PUT 108/Hydrochloride m.p. 207°–209° C.

1-amino-3-(4-methoxyphenyl)-3-phenylcyclopentane/PUT 104/Hydrochloride m.p. 230°–232° C.

EXAMPLE 2

1-dimethylamino-3,3-diphenylcyclopentane/PUB 112/

To dimethylamine (1.00 mole) at −20° C. was slowly added formic acid (0.25 mole). 3,3-diphenylcyclopentanone (0.100 mole) dissolved in N,N-dimethylformamide (100 ml) was added and the temperature allowed to rise. After boiling at 140° C. for 5 hours, the solution was cooled. Benzene and water were added and the organic phase was extracted with 1 N HCl. The acid solution was made alkaline and extracted with benzene and ether. Removal of the solvents and distillation yielded the amine (80%). B.p. 150° C./0.05 mm. M.P. 62°–64° C. Hydrochloride: M.p. 159°–160° C.

According to the method described in Example 2, the following compounds were prepared:

1-methylamino-3,3-diphenylcyclopentane/PUB 107 Hydrochloride m.p. 197°–199° C.

1-methylamino-3-(4-chlorophenyl)-3-phenylcyclopentane/PUN 125/Hydrochloride m.p. 209°–211° C.

1-dimethylamino-3-(4-chlorophenyl)-3-phenylcyclopentane/PUN 123/Hydrochloride m.p. 168°–170° C.

EXAMPLE 3

1-aminomethyl-3,3-diphenylcyclopentane/PUE 119/

3,3-diphenylcyclopentanecarboxylic acid (0.100 mole) and thionyl chloride (100 ml) were refluxed for 2 hours. Thionyl chloride was removed and the residue was dissolved in ether. Ammonia was bled in for 2 hours, ammonium chloride filtered off and washed with benzene. The solvents were removed and the residual 3,3-diphenylcyclopentanecarboxylic acid amide crystallized from benzene/ether M.p. 118°–119° C. Yield: 55%.

The above amide (0.100 mole), dissolved in tetrahydrofuran (200 ml) was added dropwise to lithium aluminum hydride (0.250 mole) in tetrahydrofuran (200 ml). The mixture was refluxed for 3 hours, cooled, water and 15% NaOH was added and the mixture filtered. The filtrate was dried, the solvent removed and the residue distilled. B.p. 143°–145° C./0.2 mm Hg. $n_D^{25} = 1.5910$. Yield 75%. Hydrochloride: m.p. 186°–187° C.

According to the method described in Example 3, the following compounds were prepared:

1-methylaminomethyl-3,3-diphenylcyclopentane/PUE 122/Hydrochloride m.p. 221°–223° C.

1-dimethylaminomethyl-3,3-diphenylcyclopentane/PUE 117Hydrochloride m.p. 220°–222° C.

EXAMPLE 4

1-amino-3,3-diphenylcyclopentane

Method D

To sodium (0.200 mole) dissolved in methanol (50 ml) was added 3,3-diphenylcyclopentanecarboxylic acid amide (0.100 mole) in methanol (30 ml). Bromine (0.100 mole) was added dropwise at 0° C. The mixture was refluxed for 15 minutes and the methanol removed. Water (100 ml) was added, the solution made alkaline with ammonia and extracted with ether and benzene. The solvents were removed and the residue was refluxed in ethanol (500 ml) and 10 N NaOH (100 ml) for 4 hours. Ethanol was removed and the aqueous phase extracted with ether.

The crude base was obtained after evaporation of the solvent. Yield: 50%.

EXAMPLE 5

1-amino-3,3-diphenylcyclopentane

Method E

To 3,3-diphenylcyclopentanecarboxylic acid (0.100 mole), in water (20 ml) and acetone (75 ml) at 10° C. was added triethylamine (0.110 mole) in acetone (75 ml). Ethylchloroformate (0.120 mole) in acetone (50 ml.) was added at 5° C. After one hour, sodium azide (1.50 mole) in water (30 ml) was added at 0° C.

After stirring at 0° C. for one hour, the mixture was poured into water (500 ml) and the aqueous phase was extracted with ether. The ether was removed and the residue was heated with 70% aqueous acetic acid at 100° C. for two hours. Concentrated hydrochloric acid was added and the mixture was heated at 100° C. for 15 hours. The solution was cooled and poured into ice water (500 ml) and made alkaline. The aqueous phase was extracted with ether and, after evaporation of the solvent, the residue was distilled. Yield: 65% B.p. 145°/0.1 mm Hg. M.p. 72°–73° C. Hydrochloride: m.p. 181°–183° C.

EXAMPLE 6

Preparation of tablets (a) Each tablet contains:

| | |
|---|---|
| 1-amino-3,3-diphenylcyclopentane-HCl | 10 mg |
| Lactose | 60 mg |
| Starch | 29 mg |
| Magnesium stearate | 1 mg |

The powders are mixed and directly compressed to tablets with a diameter of 6 mm.

The active substance shown above may be replaced by other pharmaceutically acceptable acid addition salts according to the invention.

| (b) | | |
|---|---|---|
| | 1-aminomethyl-3,3-diphenylcyclopentane | 50 mg |
| | Aerosil® (silicium dioxide) | 20 mg |
| | Lactose | 100 mg |
| | Starch | 30 mg |
| | Magnesium stearate | 2 mg |

The active principle is mixed with the Aerosil®. This mixture is added to the other powders. Tablets are compressed with a diameter of 10 mm.

The active substance shown above may be replaced by other pharmaceutically acceptable acid addition salts according to the invention.

EXAMPLE 7

Preparation of capsules

| (a) | | |
|---|---|---|
| | 1-amino-3,3-diphenylcyclopentane | 20 mg |
| | Peanut oil | 60 mg |

The solution is filled into soft gelatine capsules. Each capsule containing 20 mg of the active principle.

The active substance shown above may be replaced by other pharmaceutically acceptable acid addition salts according to the invention.

| (b) | | |
|---|---|---|
| | 1-amino-3,3-diphenylcyclopentane | 10 mg |
| | Polyoxyethylene sorbitane monooleate | 100 mg |

The capsules are made as described above.

The active substance shown above may be replaced by other pharmaceutically acceptable acid addition salts according to the invention.

PHARMACOLOGICAL METHODS

A. Biochemical Tests

1. Inhibition of the uptake of tritiated 5-HT in vitro and in vivo

The method is described by Ross and Renyi in European Journal of Pharmacology 7 (1969), 270–277. Tricyclic anti-depressant drugs of type imipramine given in vivo to mice decrease the uptake of $^3$H-5-HT in vitro. The drugs were administered intraperitoneally half an hour before the animals were killed and the midbrain was taken out and sliced and incubated in a mixture consisting of, per 100 mg of brain slices, 0.2 μmole of $^3$H-5-HT and 1 μmole of glucose in 2 ml of Krebs-Henseleit buffer, pH 7.4. The incubation time was 5 minutes with 5 minutes of preincubation before $^3$H-5-HT was added. The radioactive $^3$H-5-HT taken up in the slices was extracted with ethanol and the amount was determined by liquid scintillation. The dose producing 50% decrease of the active uptake ($ED_{50}$) was determined graphically from dose response curves. Active uptake is defined as that part of the radioactive uptake which is inhibited by a high concentration of cocaine. All doses were given at least to four animals.

2. Inhibition of the uptake of tritiated noradrenaline in vitro and in vivo

The method is found in European Journal of Pharmacology 2 (1967), 181–186. The animals were killed half or one hour after the administration of the drugs in vivo (i.p.). The slices, made from cortex, were preincubated for five minutes and incubated with 0.1 μmole per ml of $^3$H-noradrenaline for further five minutes. The incubation mixture consisted of 0.2 μmole of $^3$H-NA and the brain slices in 2 ml of Krebs-Henseleits buffer, pH 7.4. The radioactive $^3$H-NA taken up in the slices was extracted with ethanol and the amount was determined by liquid scintillation. The dose producing 50 percent decrease of the active uptake ($ED_{50}$) was determined graphically from dose response curves. At least four animals were used at each dose level.

B. Pharmacological tests 1. 5-HTP response potentiation test

Inhibition of the uptake of 5-HT potentiates the effects of administered 5-hydroxytryptophane (5-HTP) probably by increasing the amount of 5-HT at the receptor. Three mice are given the test drugs one hour (or 4, 24 hours) before dl-5-HTP 90 mg/kg i.v. 5-HTP alone gives only a weak behavioral syndrome but in pretreated mice there is seen a characteristic behavioral syndrome, which comes within five minutes: tremor, lordosis, abduction of the hindlegs, head-twitches.

These small movements are quantitatively measured in an activity box, type Animex, which can distinguish between small and gross movements. The activity is measured during 20 minutes and only in the case the animals have a fullblown syndrome. Each group consists of 3 animals and at least 4 groups were tested at 25 mg/kg i.p. Control groups receiving imipramine (Tofranil®) are used as reference, since imipramine constantly potentiated dl-5-HTP.

2. Dopa response potentiation test

Inhibition of monoamine oxidase together with blockage of the uptake of NA potentiate the effects of administrated 1-Dopa. This test is developed by G. M. Everett (Antidepressant Drugs, ed. S. Carattini, 1966).

Mice in groups of 3 are pretreated with Pargyline® 40 mg/kg p.o. about 10–16 hours before the test. The test drugs are given i.p. one or four hours before 1-Dopa 100 mg/kg i.p. The mice are observed for one hour after 1-Dopa administration. 1-Dopa gives a characteristic syndrome which is scored as follows:

1. piloerection, slight salivation, slight increased motor activity
2. piloerection, salivation, marked increased motor activity and irritability
3. piloerection, profuse salivation, marked irritability and reactivity, jumping, squeaking, fighting.

The control groups are Amitriptyline (20 mg/kg i.p. 4 hours before 1-Dopa) and saline (1 hour before 1-Dopa). Amitriptyline always scores three at this dose whereas saline gives a one score. The test drugs were all tested at 10 mg/kg i.p.

Motor activity in mice

The exploratory activity of mice was recorded in a locomotion cage in which the movements were counted each time the animals cross-circuit an electrical current in the bottom plate. The activity was recorded for ten minutes one hour after the administration of the drug. The animals were tested individually. Groups of six mice were used and the mice were only used once. The activity was expressed in percent of the activity of control groups ran simultaneously.

Acute toxicity, behavior and anticholinergic effect (mydriasis) in mice

The compounds were given by intravenous route to 3 mice. $LD_{50}$ is the dose which kills 50% of the animals within 24 hours. Seizures, gait, sedation and grip strength were recorded. Pupil width (mydriasis) which reveals peripheral anti-cholinergic action was measured in green light. These data are expressed in percent of control values 10 minutes after injection. $PD_{200}$ is the dose which increases the pupil by 200%.

Drug Induced Arrhythmia in Rats: ECG changes and $LD_{50}$

Rats were infused intravenously with test drugs and relevant reference compounds. The doses are increased stepwise. The first dose causing ECG changes of any type was noted, and thereafter the doses were increased up to the lethal dose.

it is maximal after four hours and it is still pronounced after 16 hours. Strong inhibition of the uptake of noradrenaline only is seen with compounds PUE 119 and PUE 122 and to a somewhat lower degree in PUE 117, PUB 107 and PUB 112. The uptake inhibition of the compounds of the invention having the amino nitrogen atom bound directly to the ring structure, e.g., PUN 122, PUN 123 and PUB 105 differs from the known compound imipramine in having a substantially nonselective ability towards noradrenaline. Such nonselective activity may be desirable in the treatment of certain depressive disorders, especially in those disorders which are connected with synaptical lack of both said transmittors or in cases when it is known which transmittor is lacking.

The interaction with 5-hydroxytryptophane and l-dopa correlates well with the uptake inhibition of 5-hydroxytryptamine and noradrenaline. The intravenous toxicity of the compounds is about comparable to that of imipramine. PUB 105 has much weaker peripheral anticholinergic effects than imipramine, and causes ECG changes in a dose 3 times higher than that of imipramine. These results indicate that in this series of compounds it is possible to differentiate the uptake inhibition from the unwanted side effects and to find potent inhibitors of the uptake of 5-hydroxytryptamine and/or noradrenaline in the brain.

We claim:
1. A compound of the formula

| | Inhibition (50 %) of uptake | | | | 5-HTP[3] potentiation 25 mg/kg i.p. | | L-DOPA[4] potentiation 10 mg/kg i.p. | | Motor activity $ID_{50}$ mg/kg i.p. | Mydriasis $PD_{200}$ mg/kg i.v. | Acute toxicity $LD_{50}$ mg/kg i.v. | $LD_{50}$ i.v. rat | ECG changes i.v. rat |
|---|---|---|---|---|---|---|---|---|---|---|---|---|---|
| | in vitro | | in vivo | | | | | | | | | | |
| | 5-HT[1] | NA[2] | 5-HT[1] | Na[2] | | | | | | | | | |
| Substance | μg/ml | | mg/kg i.p. | | 1h | 4h | 1h | 4h | | | | | |
| PUB 105 | 0.18 | 0.15 | 10–20[5] | 20[5] | 12.5 | 25 | 3 | 3 | >50 | 19 | 22 | 58 | 14 |
| PUB 107 | 1 | 0.7 | >40 | 20 | 0 | | 2 | 2 | >50 | 15 | 30 | | |
| PUB 112 | 0.7 | 0.4 | >40 | 25 | 25 | | 2.5 | 2 | >50 | <1 | 18 | | |
| PUE 119 | 0.34 | 0.025 | >40 | 0 | 0 | | 0 | 1.5 | 1.5 | >50 | 2.5 | 22 | |
| PUE 122 | 4.2 | 0.05 | >40 | 5.5 | 0 | | 3 | 3 | >50 | >12.5 | 15 | | |
| PUE 117 | 3.6 | 2.3 | >40 | 17 | 0 | | 3 | 1.5 | >50 | <1 | 30 | | |
| PUN 122 | 0.7 | 0.3 | 20 | 30 | 25 | | 3 | 3 | >50 | >12.5 | 15 | | |
| PUN 123 | 1 | 1 | 40 | 30 | 25 | 0 | 0 3 | 3 | >50 | <10 | 30 | | |
| PUN 125 | 2 | 1 | >40 | >40 | 0 | | 1 | 1 | | | | | |
| PUT 108 | 1 | 2.5 | >40 | >40 | >25 | | >10 | | >50 | >23 | 23 | | |
| PUT 104 | 0.5 | 1 | >40 | >40 | >25 | | >10 | | | >40 | >40 | | |
| Imipramine | 0.10 | 0.06 | 24 | 6 | 25 | 0 | 2 | 1 | 45 | 13 | 28 | 9.3 | 4.7 |

[1] 5-HT = 5-hydroxytryptamine $10^{-7}$M
[2] Na = dl-noradrenaline $10^{-7}$M
[3] 5-HTP = 1-5-hydroxytryptophane
[4] 1-DOPA = 1-3,4-dihydroxyphenyl-alanine
[5] long duration
0 = without effect

Evaluation of the results obtained in the pharmacological tests

The results are summarized in the table.

In vitro, compounds PUN 122, PUN 123, PUB 112, PUB 107, PUB 105 and PUT 104 are potent inhibitors of the uptake of both 5-hydroxytryptamine and noradrenaline. Two compounds PUE 119 and PUE 122 are strongly effective in inhibiting the uptake of noradrenaline, while having a considerably weaker effect on the uptake of 5-hydroxytryptamine. In vivo, strong inhibition of the uptake of both 5-hydroxytryptamine and noradrenaline is seen for compounds PUN 122, PUN 123 and PUB 105. Both PUN 122 and PUB 105 inhibit the uptake mechanism for a much longer time than does the reference substance imipramine. For PUB 105 and PUN 122 the uptake inhibition increases with time and

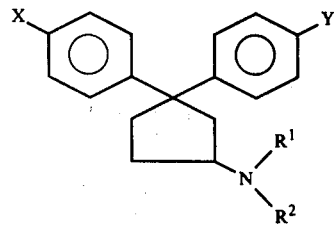

wherein X and Y are the same or different and each represents a member selected from the group consisting of a hydrogen atom, a chloro group and a methoxy group and $R^1$ and $R^2$ are the same or different and each represents a member selected from the group consisting of a hydrogen atom or a methyl group, and pharmaceutically acceptable acid addition salts thereof.

2. A compound according to claim 1 in the form of a pure isomer.

3. A compound according to claim 1 in the form of an optically pure isomer.

4. A compound according to claim 1 having the formula

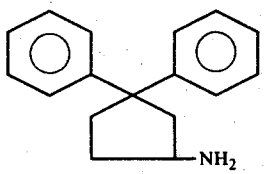

or a pharmaceutically acceptable acid addition salt thereof.

5. The (+)-enantiomer of the compound according to claim 4.

6. The (−)-enantiomer of the compound according to claim 4.

7. A compound according to claim 1 having the formula

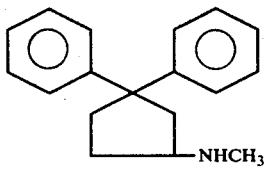

or a pharmaceutically acceptable acid addition salt thereof.

8. A compound according to claim 1 having the formula

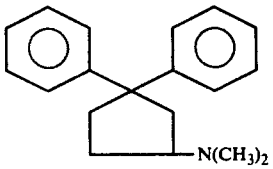

or a pharmaceutically acceptable acid addition salt thereof.

9. A compound according to claim 1 having the formula

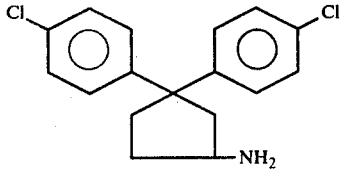

or a pharmaceutically acceptable acid addition salt thereof.

10. A compound of the formula

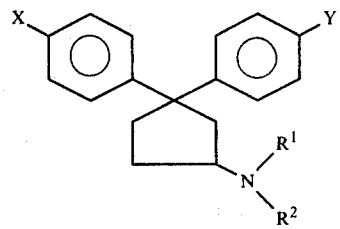

wherein X and Y are different and each represents a member selected from the group consisting of a hydrogen atom, a chloro group and a methoxy group and $R^1$ and $R^2$ are the same or different and each represents a member selected from the group consisting of a hydrogen atom and a methyl group, and pharmaceutically acceptable acid addition salts thereof.

11. A compound according to claim 10 in the form of a pure geometric isomer.

12. A compound according to claim 10 in the form of a pure optical isomer.

13. A compound according to claim 10 in the form of a pure geometric and optical isomer.

14. A compound according to claim 10 having the formula

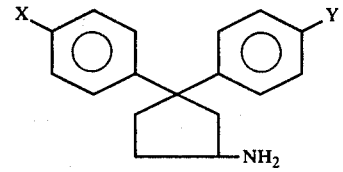

wherein one of X and Y is a chloro group and the other is a hydrogen atom, or a pharmaceutically acceptable acid addition salt thereof.

15. A compound according to claim 14 in the form of a pure geometric isomer.

16. A compound according to claim 14 in the form of a pure optical isomer.

17. A compound according to claim 14 in the form of a pure geometric and optical isomer.

18. A compound according to claim 10 having the formula

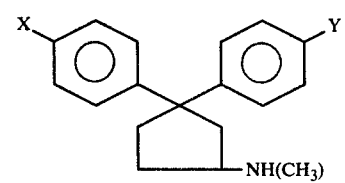

wherein one of X and Y is a chloro group and the other is a hydrogen atom, or a pharmaceutically acceptable acid addition salt thereof.

19. A compound according to claim 10 having the formula

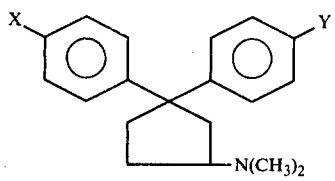

wherein one of X and Y is a chloro group and the other is a hydrogen atom, or a pharmaceutically acceptable acid addition salt thereof.

20. A compound according to claim 10 having the formula

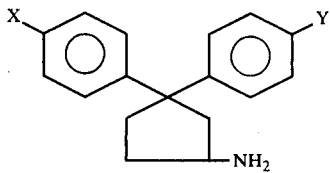

wherein one of X and Y is a methoxy group and the other is a hydrogen atom and pharmaceutically acceptable acid addition salt thereof.

21. A pharmaceutical preparation for the treatment of depression containing as an active ingredient an antidepressive effective amount of a compound of the formula

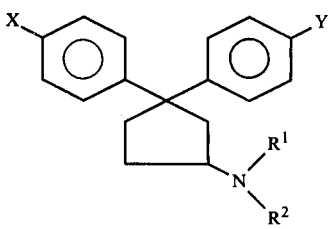

wherein X and Y are the same or different and represent a member selected from the group consisting of a hydrogen atom, a chloro group and a methoxy group and $R^1$ and $R^2$ are the same or different and are selected from the group consisting of a hydrogen atom and a methyl group, and pharmaceutically acceptable acid addition salts thereof, together with a pharmaceutically acceptable carrier.

22. A pharmaceutical preparation according to claim 21 in which the active ingredient is a compound of the formula

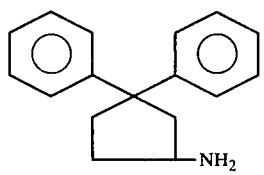

or a pharmaceutically acceptable acid addition salt thereof.

23. A pharmaceutical preparation according to claim 21 in which the active ingredient is a compound of the formula

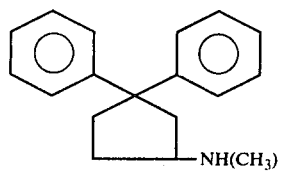

or a pharmaceutically acceptable acid addition salt thereof.

24. A pharmaceutical preparation according to claim 21 in which the active ingredient is a compound of the formula

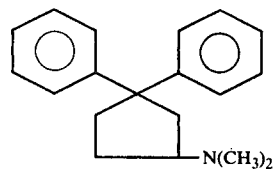

or a pharmaceutically acceptable acid addition salt thereof.

25. A pharmaceutical preparation according to claim 21 in which the active ingredient is a compound of the formula

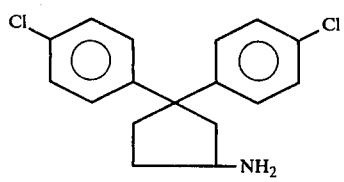

or a pharmaceutically acceptable acid addition salt thereof.

26. A pharmaceutical preparation for the treatment of depression containing an active ingredient an antidepressive effective amount of a compound of the formula

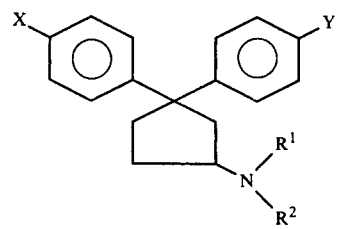

wherein X and Y are different and each represent a member selected from the group consisting of a hydrogen atom, a chloro group and a methoxy group and $R^1$ and $R^2$ are the same or different and each represent a member selected from the group consisting of a hydrogen atom and a methyl group, and pharmaceutically acceptable acid addition salts thereof, together with a pharmaceutically acceptable carrier.

27. A pharmaceutical preparation according to claim 26 in which the active ingredient is a compound of the formula

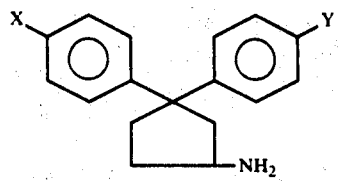

wherein one of X and Y is a chloro group and the other is a hydrogen atom, or a pharmaceutically acceptable acid addition salt thereof.

28. A pharmaceutical preparation according to claim 26 in which the active ingredient is a compound of the formula

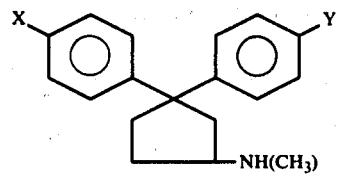

wherein one of X and Y is a chloro group and the other is a hydrogen atom, or a pharmaceutically acceptble acid addition salt thereof.

29. A pharmaceutical preparation according to claim 26 in which the active ingredient is a compound of the formula

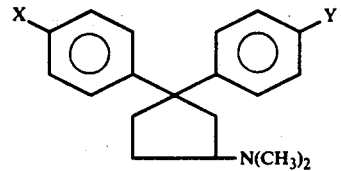

wherein one of X and Y is a chloro group and the other is a hydrogen atom, or a pharmaceutically acceptable acid addition salt thereof.

30. A pharmaceutical preparation according to claim 26 in which the active ingredient is a compound of the formula

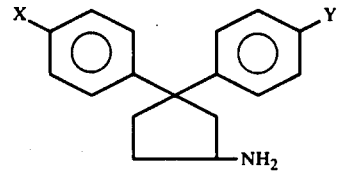

wherein one of X and Y is a methoxy group and the other is a hydrogen atom, or a pharmaceutically acceptable acid addition salt thereof.

31. A method for the treatment of depression which comprises administering to a host a pharmaceutically effective amount for the treatment of depression of a compound of the formula

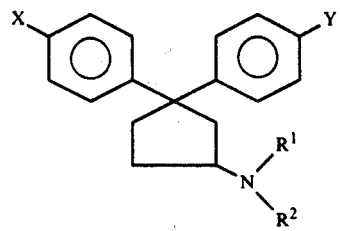

wherein X and Y are the same or different and represent a member selected from the group consisting of a hydrogen atom, a chloro group and a methoxy group and $R^1$ and $R^2$ are the same or different and are selected from the group consisting of a hydrogen atom and a methyl group, and pharmaceutically acceptble acid addition salts thereof, together with a pharmaceutically acceptable carrier.

32. A method according to claim 31 in which the compound has the structural formula

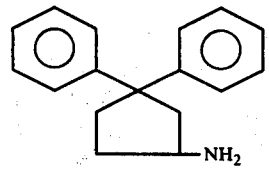

or a pharmaceutically acceptable acid addition salt thereof.

33. A method according to claim 31 in which the compound has the structural formula

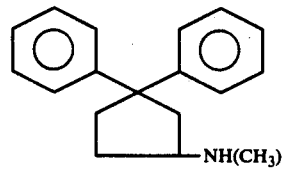

or a pharmaceutically acceptable acid addition salt thereof.

34. A method according to claim 31 in which the compound has the structural formula

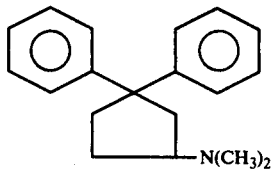

or a pharmaceutically acceptable acid addition salt thereof.

35. A method according to claim 31 in which the compound has the structural formula

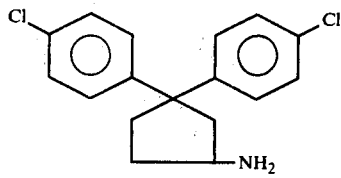

or a pharmaceutically acceptable acid addition salt thereof.

36. A method for the treatment of depression which comprises administering to a host a pharmaceutically effective amount for the treatment of depression of a compound of the formula

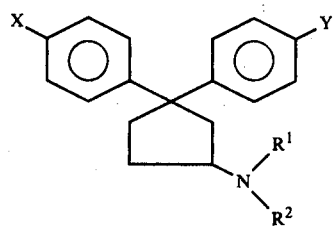

wherein X and Y are different and each represents a member selected from the group consisting of a hydrogen atom, a chloro group and a methoxy group and $R^1$ and $R^2$ are the same or different and each represents a member selected from the group consisting of a hydrogen atom and methyl group, and pharmaceutically acceptable acid addition salts thereof, together with a pharmaceutically acceptable carrier.

37. A method according to claim 36 in which the compound has the structural formula

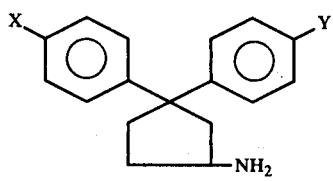

wherein one of X and Y is a chloro group and the other is a hydrogen atom, or a pharmaceutically acceptable acid addition salt thereof.

38. A method according to claim 36 in which the compound has the structural formula

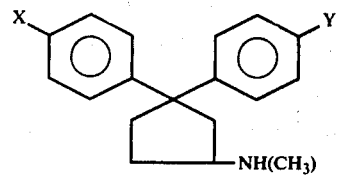

wherein one of X and Y is a chloro group and the other is a hydrogen atom, or a pharmaceutically acceptable acid addition salt thereof.

39. A method according to claim 36 in which the compound has the structural formula

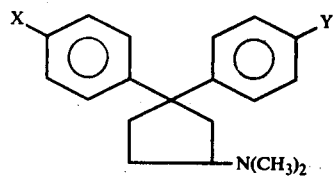

wherein one of X and Y is a chloro group and the other is a hydrogen atom, or a pharmaceutically acceptable acid addition salt thereof.

40. A method according to claim 36 in which the compound has the structural formula

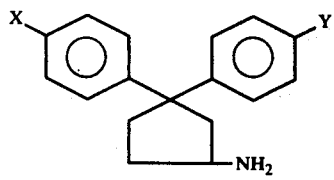

wherein one of X and Y is a methoxy group and the other is a hydrogen atom, or a pharmaceutically acceptable acid addition salt thereof.

* * * * *